United States Patent [19]

Groke

[11] 4,327,084

[45] Apr. 27, 1982

[54] AQUEOUS SOLUTION FOR INTRAVENOUS ADMINISTRATION

[75] Inventor: Karl Groke, Eggersdorf, Austria

[73] Assignee: Chemie Linz Aktiengesellschaft, Linz, Austria

[21] Appl. No.: 88,651

[22] Filed: Oct. 26, 1979

Related U.S. Application Data

[63] Continuation-in-part of Ser. No. 892,863, Mar. 31, 1978, abandoned.

[30] Foreign Application Priority Data

Jul. 8, 1977 [DE] Fed. Rep. of Germany ....... 2731013

[51] Int. Cl.³ .................... A61K 31/00; A61K 47/00; A61K 31/625; A61K 31/505
[52] U.S. Cl. .................................. 424/176; 424/229; 424/251
[58] Field of Search .................. 424/176, 229, 251

[56] References Cited

U.S. PATENT DOCUMENTS 3,551,564 12/1970 Klaui .................................. 424/229
3,592,889 7/1971 Lindvall et al. .................... 424/176
3,637,640 1/1972 Huber ................................. 424/176

OTHER PUBLICATIONS

Chemical Abstracts 61: 12009(h) (1964).

*Primary Examiner*—Jerome D. Goldberg
*Attorney, Agent, or Firm*—Wenderoth, Lind & Ponack

[57] ABSTRACT

Clear aqueous solution capable for intravenous administration comprising 2,4-diamino-5-(3',4',5'-trimethoxybenzyl)-pyrimidine as a sulphonamide potentiator, a water-soluble medicinally-acceptable salt of 3-methoxy-4-(4'-aminobenzol-sulphonamido)-1,2,5-thiadiazole and from about 5 to about 40% by weight of a compound selected from the group consisting of sugar-alcohols having 5 or 6 carbon atoms, glucose and fructose, which solution has a pH-value within the range of 6 to 8.

3 Claims, No Drawings

AQUEOUS SOLUTION FOR INTRAVENOUS ADMINISTRATION

This application is a continuation-in-part of Ser. No. 892,863, filed Mar. 31, 1978, now abandoned.

This invention relates to a sulphonamide-containing pharmaceutical composition. More particularly, the invention is concerned with medicinally acceptable aqueous solutions containing a sulphonamide and sulphonamide potentiator, which solutions are adapted for intravenous administration, especially for infusion-purposes.

It is known that the preparation of parenterally-acceptable solutions of sulphonamides and sulphonamide potentiators, such as, for example, 2,4-diamino-5-(3′,4′,5′-trimethoxybenzyl)-pyrimidine (trimethoprim) presents difficulties because of the solubility characteristics of the active ingredients, especially those of trimethoprim.

Previously, it has been proposed, in U.S. Pat. No. 3,551,564, to prepare solutions, especially for injection purposes, by dissolving a water-soluble salt of a sulphonamide in water, dissolving a sulphonamide potentiator in a water-miscible therapeutically-acceptable solvent and mixing the resulting solutions, to give a clear solution. Such a solution has the disadvantage that the non-aqueous solvent predominates in the mixture. Thus, for example, according to Example 1 of this patent only 20 ml. of water are used for 100 ml. of solution, the remainder being absolute alcohol, dimethylacetamide and polyglycol. In other Examples, the water content is reduced to 10 ml. This predominance of the organic phase is undesirable since it leads to incompatibility phenomena.

According to the process disclosed in GB-Pat. No. 1,347,472, this disadvantage is circumvented by suspending the potentiator, in a form of small-size particles, in an aqueous solution of the salt of the sulphonamide. The pH of these solutions has to be adjusted to a value of more than 9.75, preferably to 10 to 10.5. The preparation is therefore suitable only for veterinary medicine.

On the other hand, U.S. Pat. No. 3,985,876 discloses a process wherein it is only possible to prepare solutions in the acid pH range, namely having a pH value of from 2 to 7, preferably from 4 to 5. In this process, the sulphonamide is dissolved in a pharmaceutically acceptable, water-miscible, organic solvent and mixed with a solution of monoaddition salt of an acid and trimethoprim. Apart from the pH value of the solution being unacceptable, above all for infusion purposes, the process again requires a substantial proportion of organic solvent, amounting to 50% of more.

Surprisingly, it has now been found that it is possible to prepare solutions, on a purely aqueous basis (that is, without using any organic solvent) and having a pH within an acceptable physiological range, of a sulphonamide and 2,4-diamino-5-(3′,4′,5′-trimethoxybenzyl)-pyrimidine as the sulphonamide potentiator, the said solutions being suitable for intravenous administration by using 3-methoxy-4-(4′-aminobenzol-sulphonamido)-1,2,5-thiadiazole as the sulphonamide and dissolving the sulphonamide potentiator in water or in an aqueous solution of the sulphonamide salt, to which there has been added a certain amount of a sugar alcohol and/or of glucose and/or fructose. The resulting solution has the advantage that it is medicinally acceptable since the pH value may be adjusted, as desired, within the physiological range of 6 to 8. Thus, it is possible, without difficulty, to maintain the particularly advantageous pH value of 7.4 with these solutions. This is particularly important when the solutions are used for infusion purposes. When they are used as an infusion, there is the further advantage that the added sugar alcohols or sugars are not only well tolerated but also, in most cases, may serve as nutrients.

Accordingly, the present invention provides a pharmaceutical composition, comprising a clear, aqueous solution capable for infusion by intravenous administration, said solution comprising from about 0.1 to about 1% w/v of 3-methoxy-4-(4′-aminobenzol-sulphonamido)-1,2,5-thiadiazole as a medicinally-acceptable basic water-soluble salt, from about 0.02 to about 0.15% w/v of 2,4-diamino-5-(3′,4′,5′-trimethoxybenzyl)-pyrimidine, from about 5 to about 20% w/b of a sugar compound selected from the group consisting of sorbitol, xylitol, mannitol, glucose, fructose and a mixture of glucose and fructose, and water, said solution having a pH value within the range of 6 to 8, with the proviso that said composition does not contain any organic solvent.

The pharmaceutical composition as described above is prepared by dissolving 2,4-diamino-5-(3′,4′,5′-trimethoxybenzyl)-pyrimidine, a sulphonamide potentiator, in an aqueous solution containing at least 5% by weight of sorbitol, xylitol, mannitol, glucose or fructose or mixtures of glucose and fructose, adding to the sulphonamide potentiator solution a water-soluble, medicinally-acceptable salt of 3-methoxy-4-(4′-aminobenzol-sulphonamido)-1,2,5-thiadiazole, either (i) by dissolving it in the water used to prepare the sulphonamide potentiator solution, before adding the other constituents, or (ii) in the form of an aqueous solution; bringing the content of the sugar alcohol or glucose and/or fructosee in the final solution to 5 to 20% by weight, and thereafter, if necessary, adjusting the pH value of the solution to a value within the range from 6 to 8, preferably to a value of 7.4.

Sorbitol, xylitol or mannitol are used as the sugar alcohols, the first two being, at the same time, also nutrients. The sugars glucose and fructose may be used separately or as a mixture. A mixture of these two sugars known as invertose, which is obtained on scission of sucrose, also may be used.

The amount of the sugar alcohols and/or sugars, within the limits defined herein, depends on the desired concentration of sulphonamide potentiator and hence also of sulphonamide in the solution to be prepared. In general, the amount of sulphonamide potentiator which remains in solution is proportional to the concentration of sugar alcohol or sugar. However, there are also differences in solvent power between the various sugar alcohols or sugars to be employed according to the invention. Thus, for example, when using xylitol, more of the active compound may be dissolved in a given volume of water than when using the same amount of mannitol or sorbitol.

In the case of infusions, a content of 10% by weight of the sugar alcohol or sugar additive according to the invention, in the solution, as a rule suffices to achieve the desired active compound concentration. Since, however, most of the additives according to the invention are also nutrients, the amount thereof used will depend also on the amount of nutrient desired in the solution. This means that under certain circumstances, the selected content of sugar alcohols and/or sugars in the solution may be higher than ordinarily would be necessary to achieve a clear solution. A particular level of nutrient content below the amount required to achieve solution may be obtained, for example, by combining the sugar alcohol mannitol, which is not a nutrient, with the nutrients xylitol, sorbitol, glucose or fructose.

The aqueous solution of the salt of the sulphonamide used according to the invention can be prepared by dissolving an appropriate medicinally acceptable salt of this sulphonamide in water. It is also possible to combine the process for preparing the sulphonamide salt with the process for preparing the solution by reaction of the sulphonamide with bases in aqueous solution. Substances that can be used to form such salts are, for example, all alkalis, preferably sodium hydroxide and organic amines, preferably alkanolamines, such as ethanol amine, tri(hydroxymethyl)aminomethane and diethanolamine.

The injectable solution has to be given in an amount such that the sulphonamide is present in an effective antibacterial or antiprotozoal treatment amount and in which the sulphonamide potentiator is present in an effective sulphonamide potentiating amount.

Usually the ratio of sulphonamide to sulphonamide potentiator for obtaining a therapeutic effect is of the order of 5:1 (w/w), though other ratios, for example between 10:1 and 1:1 (w/w) are also useful.

Doses for having an effective amount of the sulphonamide 3-methoxy-4-(4'-aminobenzol-sulphonamido)-1,2,5-thiadiazole vary according to the species of the host, its size, its age and general condition of health and on the other hand depends on severity and type of infection. Conveniently daily doses of this sulphonamide of from 800 mg up to 1200 mg or, in some cases up to 1600 mg may be used. For children the doses are lower, for example of from 200 mg per day to 600 mg/day. If the ratio of sulphonamide to sulphonamide potentiator of 5:1 (w/w) is used this corresponds to daily doses of potentiator of from 40 mg/day (children) to 480 mg or 640 mg/day respectively (adults). Preferably the solutions according to the invention are used for infusion purposes and in such case preferably solutions are used which contain from about 0.1% to about 1% (w/v) of 3-methoxy-4-(4'-aminobenzol-sulphonamido)-1,2,5-thiadiazole in the form of its medicinally acceptable water soluble salts, from about 0.02% (w/v) to about 0.15 (w/v) of 2,4-diamino-5-(3',4',5'-trimethoxybenzyl)-pyrimidine and from about 5 to about 20% (w/v) of the sugar alcohol or the sugar. The remainder is water. Infusion units can be made having for example a volume of 100 ml or 250 ml.

The solutions according to the invention may be processed further in accordance with conventional methods to give infusions or injection ampoules. If sugar alcohols are used as the additives according to the invention, any conventional sterilization technique may be employed. On the other hand, when using glucose or fructose as the additive according to the invention, it is to be noted that on sterilization at temperatures above 90° C. a dark coloration occurs, due to the occurrence of the Maillard reaction. However, for such solutions all the customary techniques which work at lower temperatues are available, eg. sterile filtration or tyndallization.

The following Examples illustrate the invention and the manner in which it may be performed.

EXAMPLE 1

320 mg. of 3-methoxy-4-(4'-aminobenzol-sulphonamido)-1,2,5-thiadiazole and 44.72 mg of sodium hydroxide are dissolved in 90 ml. of water at a temperature of 80° C. to form an aqueous solution of the sodium salt, and 7,000 mg. of sorbitol and 64 mg. of 2,4-diamino-5-(3',4',5'-trimethoxybenzyl)-pyrimidine are added to this solution, to form a clear solution.

The pH of the solution is adjusted to a value of 7.4 by adding 0.55 ml. of 0.1 N hydrochloric acid, after which the solution is made up to a volume of 100 ml. with water.

After sterilization, the solution thus obtained is suitble for infusion purposes.

To obtain an infusion solution of the same concentration but having a volume of 250 ml., 800 mg. of the sulphonamide, 111.8 mg. of sodium hydroxide, 17,500 mg. of sorbitol and 160 mg. of 2,4-diamino-5-(3',4',5'-trimethoxybenzyl)-pyrimidine are employed, and are processed as described above.

EXAMPLE 2

1,600 mg. of 3-methoxy-4-(4'-aminobenzol-sulphonamido)-1,2,5-thiadiazole and 223.6 mg. of sodium hydroxide are dissolved in 200 ml. of water at a temperature of 80° C. After adding 25,000 mg. of xylitol, 320 mg. of trimethoprim are dissolved in the mixture. After adding 1.375 ml. of 0.1 N hydrochloric acid to bring the pH value to 7.4, the solution is made up to 250 ml. After conventional sterilization, it may be employed as an infusion solution.

EXAMPLE 3

3.20 g. of 3-methoxy-4-(4'-aminobenzol-sulphonamido)-1,2,5-thiadiazole and 0.45 g. of sodium hydroxide are dissolved in 850 ml. of water at a temperature of 80° C. to form an aqueous solution of the sodium salt and 100 g. of mannitol and 0.64 g. of 2,4-diamino-5-(3',4',5'-trimetnoxybenzyl)-pyrimidine are added to this solution, to form a clear solution.

The pH of the solution is adjusted to a value of 7.4 by adding 0.1 N hydrochloric acid, after which the solution is made up to a volume of 1,000 ml. with water.

After tyndallization, the solution thus obtained is suitable for infusion purposes.

EXAMPLE 4

From 3.20 g. of 3-methoxy-4-(4'-aminobenzol-sulphonamido)-1,2,5-thiadiazole, 0.45 g. of sodium hydroxide, 100 g. fructose, 0.64 g. of 2,4-diamino-5-(3',4',5'-trimethoxybenzyl)-pyrimidine and 850 ml. water a clear solution is formed as described in example 3. The pH of the solution is adjusted to a value of 7.4 with 0.1 N hydrochloric acid and then the solution is made up to a volume of 1,000 ml. with water.

After tyndallization, the solution thus obtained is suitable for infusion purposes.

EXAMPLE 5

3.20 g. of 3-methoxy-4-(4'-aminobenzol-sulphonamido)-1,2,5-thiadiazole and 0.45 g. of sodium hydroxide are dissolved in 800 ml. of water at a temperature of 80° C. and under nitrogen atmosphere to form an aqueous solution of the sodium salt and 150 g. of glucose and 0.64 g. of 2,4-diamino-5-(3',4',5'-trimethoxybenzyl)-pyrimidine are added to this solution, to form a clear solution, whereby the nitrogen atmosphere is maintained.

The pH of the solution is then adjusted to a value of 7.4 by adding 0.1 N hydrochloric acid, after which the solution is made up to a volume of 100 ml. with water.

After sterilfiltration, the solution thus obtained is suitable for infusion purposes.

EXAMPLE 6

From 3.20 g. of 3-methoxy-4(4'-aminobenzol-sulphonamido)-1,2,5-thiadiazole, 0.45 g. of sodium hydroxide, 200 g. invertose, obtained on scission of sucrose consisting of 100 g. fructose and 100 g. glucose, 0.64 g. 2,4-diamino-5-(3',4',5'-trimethoxybenzyl)-pyrimidine and water 1,000 ml. of an aqueous solution is prepared as described in example 5.

After sterilfiltration the solution may be employed as an infusion solution.

What we claim is:

1. A pharmaceutical composition comprising a clear, aqueous solution capable for infusion by intravenous administration, said solution comprising from about 0.1 to about 1% w/v of 3-methoxy-4-(4'-aminobenzol-sulphonamido)-1,2,5-thiadiazole as a medicinally-acceptable basic water-soluble salt, from about 0.02 to about 0.15% w/v of 2,4-diamino-5-(3',4',5'-trimethoxybenzyl)-pyrimidine, from about 5 to about 20% w/v of a sugar compound selected from the group consisting of sorbitol, xylitol, mannitol, glucose, fructose and a mixture of glucose and fructose, and water, said solution having a pH value within the range of 6 to 8, with the proviso that said composition does not contain any organic solvent.

2. A pharmaceutical composition according to claim 1, which has a pH value of 7.4.

3. A method of treating a mammal suffering from bacterial or protozoal infection which comprises intravenously administering to said mammal a therapeutically effective antibacterial or antiprotozoal treatment amount of the pharmaceutical composition of claim 1.

* * * * *